United States Patent [19]

Chang et al.

[11] Patent Number: 5,591,599
[45] Date of Patent: Jan. 7, 1997

[54] METHOD FOR DETECTING ANTIMICROBIAL COMPOUNDS

[75] Inventors: Tsung C. Chang, Taoyuan; Hui C. Chen, Miaoly, both of Taiwan

[73] Assignee: Food Industry Research and Development Institute, China

[21] Appl. No.: 250,285

[22] Filed: May 27, 1994

[51] Int. Cl.$^6$ .................................................. C12Q 1/18
[52] U.S. Cl. ............................................ 435/32; 435/29
[58] Field of Search .............................. 435/29, 32, 832

[56] References Cited

U.S. PATENT DOCUMENTS

| | | | |
|---|---|---|---|
| 4,321,322 | 3/1982 | Ahnell | 435/34 |
| 4,381,343 | 4/1983 | Citri | 435/24 |
| 4,946,777 | 8/1990 | Lameris et al. | 435/29 |
| 4,965,193 | 10/1990 | Chen | 435/32 |

FOREIGN PATENT DOCUMENTS

| | | | |
|---|---|---|---|
| 1520733 | 8/1978 | United Kingdom | 27/56 |
| 1585067 | 2/1981 | United Kingdom | 27/6 |
| 2063911 | 6/1981 | United Kingdom | 1/2 |
| 2211615 | 7/1989 | United Kingdom | 27/6 |

OTHER PUBLICATIONS

Okigbo et al. J of Food Protection vol. 48, No. 11 pp. 979–981 (1985).

Goldstein et al. Calculus and its Applications Prentice Hall, NJ. (1977) (pp. 53–75).

Firstenberg–Eden, R., "Rapid Estimation of the Number of Microorganisms in Raw Meat by Impedance Measurement", Institute of Food Technologies, Jan. 1983.

Okigbo et al., "Detection of Penicillin and Streptomycin in Milk by Impedance Microbiology", Journal of Food Protection, vol. 48 No. 11, pp. 979–981, Nov. 1985.

*Primary Examiner*—Esther Kepplinger
*Assistant Examiner*—Lien Tran
*Attorney, Agent, or Firm*—Fish & Richardson P.C.

[57] ABSTRACT

A method for determining the possible presence of an antimicrobial compound in a sample. The method includes the steps of: (i) adding the sample to a culture medium; (ii) growing a microorganism in the culture medium, the growth of the microorganism being susceptible to inhibition by the compound; (iii) measuring an electrical parameter of the culture medium over a period of time; (iv) determining a first time point at which an accelerating change of the electrical parameter occurs, the change resulting from the growth of the microorganism; and (v) comparing the first time point with a plurality of time points to determine the possible presence of the compound. Each of the plurality of time points is determined in a manner identical to that in which the first time point is determined except that the compound is present in the culture medium at a known concentration, and, further, a relationship exists between the plurality of time points and their corresponding concentrations. Also disclosed is a method for testing the resistance of a microorganism to an antimicrobial compound.

20 Claims, 2 Drawing Sheets

METHOD FOR DETECTING ANTIMICROBIAL COMPOUNDS

BACKGROUND OF THE INVENTION

Antimicrobial compounds, such as antibiotics and drugs, have been used as a part of dairy cattle management for several decades. Unfortunately, antimicrobial compounds used in treatments may enter the milk supply. Once present in milk, they are difficult to eliminate, and their presence is of public health concern.

An estimated 5 to 10% of American adults are hypersensitive to antibiotics. After ingestion, as little as 0.003 IU of penicillin G may cause allergic responses. The antibiotic residues also may create an environment that is favorable for resistant bacterial strains. The presence of antibiotics in milk has .also created problems in the dairy industry, including inadequate curdling of milk, improper ripening of cheeses, and decreased acid or flavor production. A 50% inhibition of cheese and yogurt starter cultures by 0.2 IU/ml of penicillin was reported. The FDA considers antibiotic-contaminated milk to be adulterated. Therefore, the test of antimicrobial compounds, such as antibiotics, in milk is important for the dairy industry.

The sensitivities of several currently used methods for the detection of penicillin G in milk are the *Sarcinia lutea* cylinder-plate method, 0.02 IU/ml; Penzyme test, 0.01 IU/ml; *Bacillus stearothermophilus* disc assay, 0.005 IU/ml; Charm test, 0.005 IU/ml; and Delvotest-P, 0.005 IU/ml. For the detection of trace residues (<0.005 IU/ml) of penicillin G in milk, a more sensitive, and preferably automatic, method is needed.

The changes in electrical properties of the culture media have been utilized for the rapid estimation of total, mesophilic, and psychrotrophic counts, coliforms, salmonella, abnormal milk, and bacteriophage in Cheddar cheese making. Electrical change was also used as a growth index of lactic acid bacteria in milk.

Okigbo and Richardson reported an impedance method using a Bactometer 123 impedance instrument to detect streptomycin or penicillin G in sterile milk inoculated with 5% active or 5% inactive lactic culture. Okigbo, O. N., and G. H. Richardson (1985), Detection of penicillin and streptomycin in milk by impedance microbiology, J. Food Protection, 48:979, which is hereby incorporated by reference. Although the test is more sensitive (0.001 IU/ml) than previously reported tests, quantitative results were not obtained.

SUMMARY OF THE INVENTION

An aspect of this invention relates to a method for determining the possible presence of an antimicrobial compound in a sample. By "antimicrobial compound" is meant any compound (an antibiotic or otherwise) which is capable of inhibiting the growth of a bacterium or a fungi.

The method includes the steps of: (i) adding the sample to a culture medium; (ii) growing a microorganism, e.g., a bacterium or fungi (spores or cells), in the culture medium, the growth of the microorganism being susceptible to inhibition by the compound; (iii) measuring an electrical parameter, e.g., conductance, impedance or capacitance, of the culture medium over a period of time; (iv) determining a first time point at which an accelerating change of the electrical parameter occurs (detection time, or "DT"), the change resulting from the growth of the microorganism; and (v) comparing the first time point with a plurality of time points to determine the possible presence of the compound. Each of the plurality of time points is determined in a manner identical to that in which the first time point is determined except that the compound is present in the culture medium at a known concentration, and, further, a relationship exists between the plurality of time points and their corresponding concentrations.

In a preferred embodiment of the above method, the first time point is further compared with a second time point which is determined in a manner identical to that in which the first time point is determined except that a reagent capable of abolishing the antimicrobial activity of the compound is added to the culture medium, thereby confirming the presence of the compound. For example, when the compound to be detected is a lactam antibiotic (e.g., penicillin G), β-lactamase can be use to inactivate any lactam antibiotic present in the culture medium before the second time point is determined.

Another aspect of this invention relates to a method for testing the resistance of a microorganism (e.g., bacterium) to an antimicrobial compound, the method comprising the steps of: (i) growing a microorganism to be tested in a culture medium containing the compound at a given concentration; (ii) measuring an electrical parameter of the culture medium, e.g., conductance, over a period of time; (iii) determining a first time required for an accelerating change of the electrical parameter resulting from the growth of the tested microorganism to occur (detection time, or "DT"); and (iv) comparing the first time with a second time which is determined in a manner identical to that in which the first time is determined except that the compound is absent from the culture medium. The tested microorganism is defined to be resistant to the compound when the first time is equal to the second time at the given concentration of the compound, and is defined to be not resistant to the compound when the first time is greater than the second time.

The antimicrobial compound-detecting method can be used to detect lactam antibiotics at low concentrations, e.g., as low as 0.00016 IU/ml for penicillin G, which is about 30 times more sensitive than several currently used methods. In addition, the measurement of the electrical parameter is fully automatic, and multiple samples (e.g., 120 or 240) can be analyzed simultaneously.

Other features and advantages of the present invention will be apparent from the following drawings and description of the preferred embodiments, and also from the appending claims.

BRIEF DESCRIPTION OF THE DRAWING

The drawings are first described.

DESCRIPTION OF THE PREFERRED EMBODIMENTS

Figure 1:
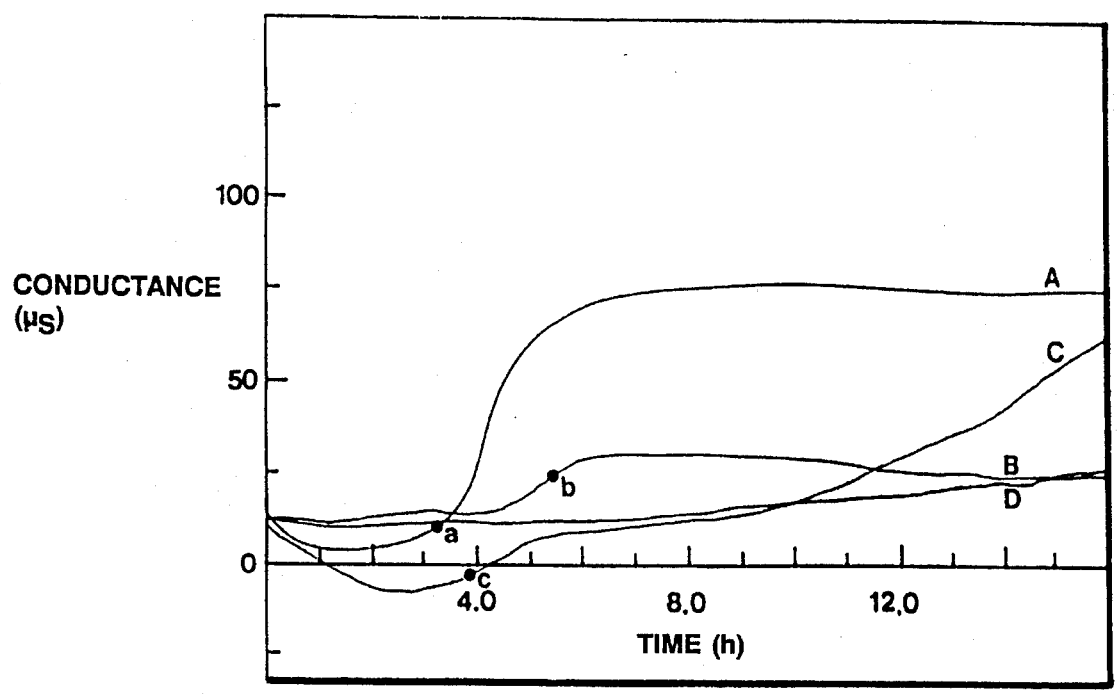
FIG. 1 is a graph showing conductance curves using four different media containing *Bacillus stearothermophilus* spores.

The method of this invention for detecting antimicrobial compounds is based on the inhibition of an antimicrobial compound on the growth of a microorganism. The change of an electrical parameter in a culture medium containing both the sample and the microorganism was continuously monitored by a microbiological analyzer, and the detection time (i.e., the inflection point of the curve obtained by plotting electrical parameter as a function of time) is delayed when an antimicrobial compound is present in the sample. The DT can be determined either automatically using software or manually from an electrical parameter-time curve. In general, the higher the concentration of the antimicrobial compound, the greater the DT. Within a certain range, there is indeed a linear relationship between the DT and the concentration of the antimicrobial compound.

The above method is highly sensitive. However, it is possible to reduce the sensitivity of this method by modifying the assay conditions (e.g., media, microorganism concentrations, incubation temperatures, or even test microorganisms) to achieve a lower sensitivity for practical use in the dairy industry. This method can also be used as a rapid screen test by setting an appropriate DT for the negative samples; samples with a DT higher than the preset DT would be considered as containing an antimicrobial compound. Of course, a buffer range should be considered in setting such a DT threshold to allow for experimental imprecision.

Another method of this invention can be used to determine whether a microorganism is resistant to a given antimicrobial compound by comparing the DT's obtained by growing the microorganism in the presence and absence of the antimicrobial compound, respectively.

In the following example, a conductimetric assay for detecting penicillin G in milk using a Malthus 2000 microbiological analyzer (Malthus Instruments Limited, Crawley, England) with *B. stearothermophilus* as the test organism was performed. However, measurement of impedance or capacitance, rather than conductance, is also feasible. For example, a Bactometer available from Vitek systems, Hazelwood, MS, U.S.A. can be used to measure conductance, capacity and impedance. Similarly, while *B. stearothermophilus* was used as the test microorganism in the following example, it can be replaced by certain other microorganisms. As an example, *Sarcinia lutea* is known to be sensitive to antibiotics of the β-lactam family (e.g., cephaprin, cloxicillin and penicillin) and therefore can also be used to detect penicillin G or its analogs. To be sure, the assay of this invention is capable of detecting all kinds of antimicrobial compounds as long as proper test microorganisms and test conditions are selected.

In this context, it should be pointed out that since *B. stearothermophilus* is also sensitive to other antimicrobial compound families including the tetracycline family (e.g., tetracycline, chlortetracycline and oxytetracycline), the erythromycin family (e.g., erythromycin, lincomycin and clindamycin), the aminoglycoside family (e.g., streptomycin), the novobiocin family (e.g., novobiocin), the chloramphenicol family (e.g., chloramphenicol) and the sulfonamide family (e.g., sulfamethazine, sulfamethoxazole and sulfisoxazole) [See Charm, S. E. and Chi, R., 1988, Microbial receptor assay for rapid detection and identification of seven families of antimicrobial drugs in milk: collaborative study, J. Assoc. Off. Anal. Chem. 71: 304, hereby incorporated by reference], the assay of this invention can also be used to detect these compounds in samples using *B. stearothermophilus* as the test microorganism.

Without further elaboration, it is believed that one skilled in the art can, based on the description herein, utilize the present invention to its fullest extent. The specific embodiment described in the following example is, therefore, to be construed as merely illustrative, and not limitative of the remainder of the disclosure in any way whatsoever.

Materials

Trypticase soy agar and trypticase soy broth were from BBL (Becton Dickinson, Cockeysville, Md.). SPYE broth (catalog number 490-001) was a product of Malthus Instruments (Crawley, England). *Bacillus stearothermophilus* ATCC 10149 spore suspension (catalog number 1801-60-6), Bacto-PM positive control medium (nonfat dry medium containing 0.12 IU of potassium penicillin; catalog number 1802-33-9), Bacto-PM negative control medium (inhibitor-free nonfat dry medium; catalog number 1803-63-1), Bacto-PM indicator agar (catalog number 1800-15-3), and Penicillin G were obtained from Difco Laboratories (Detroit, Mich.). β-lactamase (EC 3.5.2.6; catalog number P-0389) was a product of Sigma (St. Louis, Mo.).

Optimization of Conditions for Conductance Measurement

A successful conductimetric method depends on the quality of curves that are influencing by the specific sample and medium combinations. A conductance curve of good quality should exhibit a stable baseline, followed by a sharp accelerating slope and a high peak value. See Firstenberg-Eden, R., and G. Eden (1984) Impedance Microbiology, John Wiley & Sons Inc., New York, N.Y., which is hereby incorporated by reference. Because some metabolite end-products will yield a stronger conductance signal, the selection of an appropriate medium is crucial.

In this example, conductance changes, as measured in microsiemens (μS), were automatically monitored and graphically represented by the software package of a Malthus 2000 microbiological analyzer (Malthus Instruments Limited, Crawley, England). To obtain a conductance curve of good quality (i.e., a curve having a stable baseline, a sharp slope, and a high conductance value), four different media (trypticase soy broth, trypticase soy agar, SPYE broth, and Bacto-PM indicator agar) were used for the inoculation of *B. stearothermophilus* spores. The media were autoclaved at 121° C. for 15 min and seeded with spores to give a concentration of 1% (1 ml of stock spore suspension added to 100 ml of sterile medium; final concentration about $10^6$ spores/ml). The media containing the spores were then dispensed in 2-ml amounts in 5-ml capacity conductance cells and then incubated at 55° C. in the water bath of the Malthus 2000 microbiological analyzer. Readings of conductance for each cell were taken every 6 min over 24 h. Results were obtained numerically as conductance data or graphically as conductance growth curves. Detection time ("DT") in hours for each cell was automatically determined by the instrument software when conductance values increased by 1 μS or more for three consecutive scans. The results are shown in FIG. 1.

The four curves of conductance change in FIG. 1 (A, B, C and D) were obtained from the use of PM indicator agar, trypticase soy broth, tryptic soy agar, and SPYE broth, respectively, as the media. The letters a, b, and c are the detection times of curves A, B, and C; curve D does not have a measurable detection time. As illustrated in FIG. 1, PM indicator agar met the criteria for a good quality curve. In addition, the amplitude of conductance generated by PM indicator agar was at least twice those obtained by the other three media. Therefore, PM indicator agar was selected as the medium for further tests.

Figure 2:
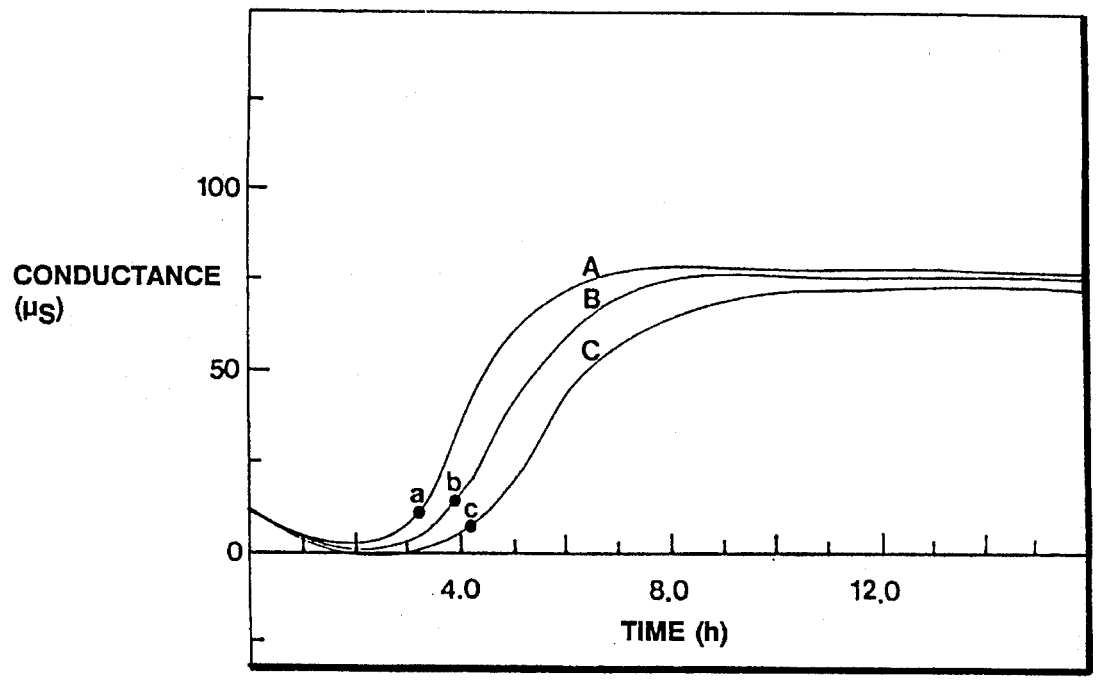
FIG. 2 is a graph showing conductance curves using PM indicator agar containing three inoculum concentrations of *Bacillus stearothermophilus* spores.

Although 1% (about $10^6$ spores/ml) of spore suspension is generally recommended for the *B. stearothermophilus* disc assay, this concentration might not be suitable for the conductance methodology. Three inoculum percentages were used in the PM indicator agar to evaluate the influence of inoculum on the conductance curves, and the results are shown in FIG. 2. Curves A, B, and C in FIG. 2 stand for conductance changes from PM indicator agar containing three inoculum concentrations of *Bacillus stearothermophilus* spores: A, 1% ($10^6$ spores/ml); B, 0.1% ($10^5$ spores/ml); and C, 0.01% ($10^4$ spores/ml). The letters a, b, and c are the detection times of curves A, B, and C, respectively. As shown in FIG. 2, spore concentration had little effect on the curve quality except that the DT was inversely proportional to the spore concentrations used. The DT's were 3.3, 3.9, and 4.2 h for spore concentrations of 1, 0.1 and 0.01%, respectively. However, the three conductance curves showed the same trend of conductance change and had similar peak values of conductance, regardless of the initial spore load. Because time is an important factor for the quality control of milk, 1% spore concentration was used in the following experiments.

Relationship between Detection Time and Penicillin G Concentration

Experiments were performed to determine the effect of Penicillin G on conductance curves and the sensitivity of this conductimetric method.

The positive control medium containing 0.12 IU of penicillin G (Difco) was serially diluted twofold with the negative control medium (Difco) to obtain samples containing decreasing concentrations of the antibiotic. Following the addition of 1 ml of each diluted positive control medium into the conductance cell (six replicates), 2 ml of 50° C. PM indicator agar containing 1% spore suspension were added to each cell, mixed thoroughly, and incubated at 55° C. for the monitoring of conductance change. The sensitivity of the conductimetric assay was defined as the concentration of penicillin G that had a DT value higher than the negative control at a significant level of 0.01, using the t test. The results are shown in FIG. 3.

Figure 3:
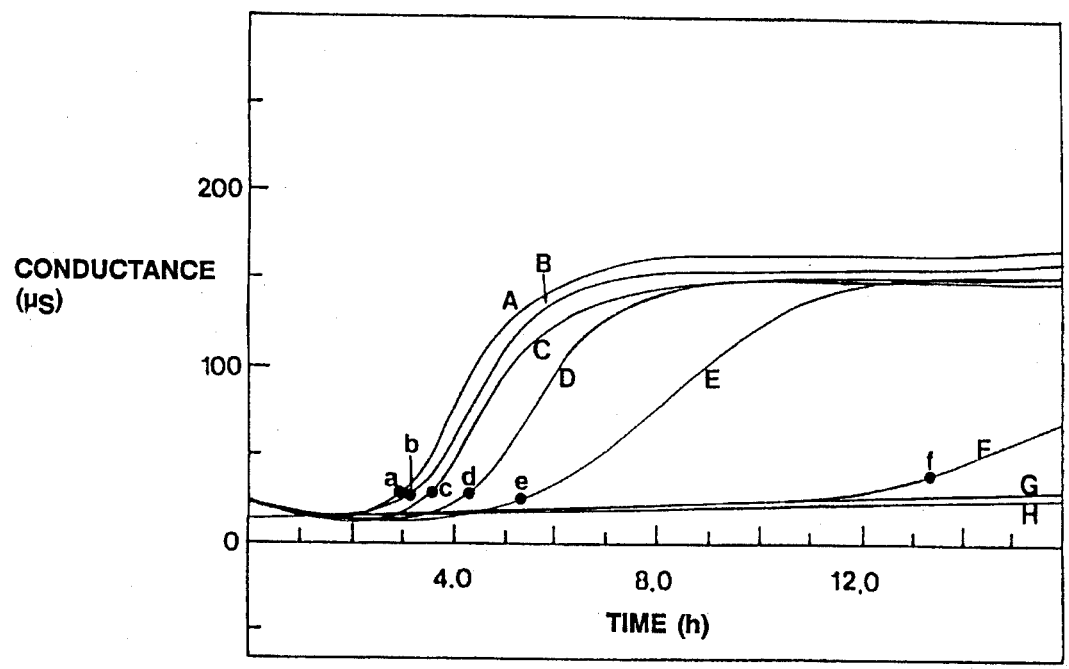
FIG. 3 is a graph showing conductance curves of reconstituted nonfat dry milk samples containing different concentrations of penicillin G.

In FIG. 3, conductance curves A, B, C, D, E, F, G and H correspond to samples containing 0 IU/ml, 0.00008 IU/ml, 0.00016 IU/ml, 0.00031 IU/ml, 0.00062 IU/ml, 0.00125 IU/ml, 0.0025 IU/ml, and 0.005 IU/ml of penicillin G, respectively. The letters a, b, c, d, e, and f denote the respective detection times of curves A, B, C, D, E, and F. Obviously, the higher the concentration of penicillin G was, the longer the DT. The negative control had a DT of 3.1 h. As concentration of the antibiotic increased, the DT was higher, and the slope of the conductance curve was smaller. When the concentration of penicillin G was $\geq 0.0025$ IU/ml (FIG. 3; curves G and H), the inhibition of the growth of *B. stearothermophilus* was so strong that a level line of curve was obtained. Under this condition, no DT could be obtained during a 24-h incubation period. At a penicillin G concentration of 0.0012 IU/ml (FIG. 3; curve F), the slope of the curve was so small that it was difficult to assign a correct DT. Inevitably, the DT of the negative and positive controls may be subject to change, because the physiological state and the concentration of the spore suspension are difficult to maintain at fixed values between lots and between experiments. However, in many separate experiments, the DT of negative control was always between 2.6 to 3.2 h.

In testing a serially diluted positive samples, the DT's of samples containing penicillin G higher than 0.005 IU/ml could not be completely restored to the value of negative control by β-lactamase (final concentration 15 U/ml) treatment at 37° C. for 30 min. This might be due to the incomplete digestion of penicillin G by the enzyme under the conditions used. The complete reversal could be achieved by proper dilution of samples with penicillin G concentrations >0.005 IU/ml.

The sensitivity of the conductimetric assay for penicillin G was 0.00016 IU/ml; at this concentration the DT (mean of six replicates) was 3.38 h that was significantly higher ($\alpha=0.01$) than the negative control (DT 3.11 h).

Figure 4:
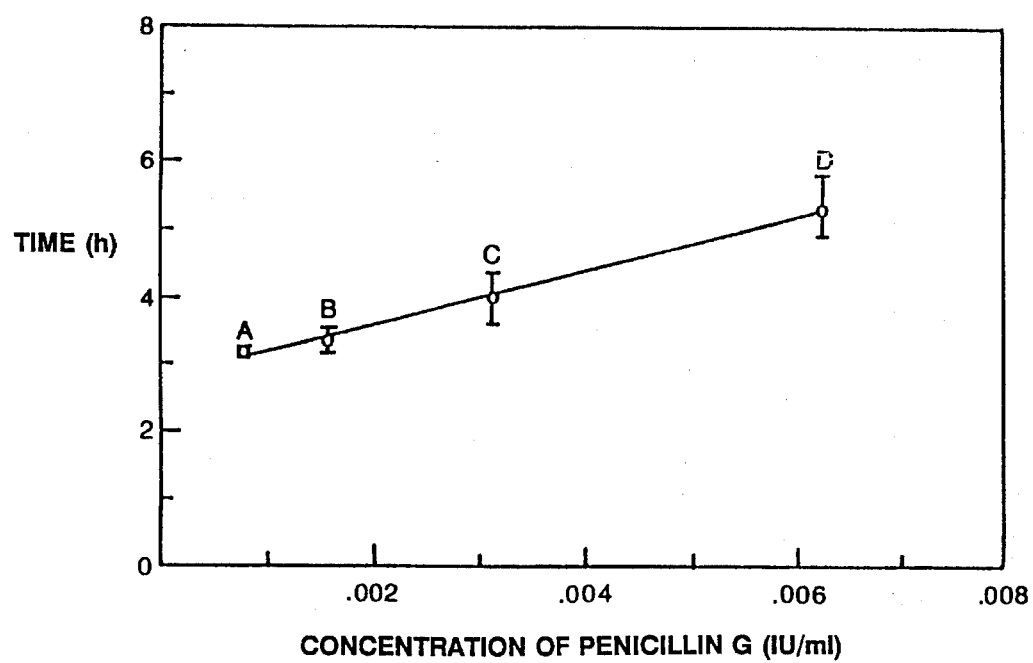
FIG. 4 is a graph showing a linear relationship between detection time ("DT") and penicillin G concentration in nonfat dry milk samples.

As shown in FIG. 4, a linear regression line ($r=0.99$) correlating the DT (in hours; six replicates) and the concentration (international units per ml) of penicillin G exists: A, 0.00008 IU/ml (DT 3.18±0.07 h); B, 0.00015 IU/ml (DT 3.38±0.18 h); C, 0.00031 IU/ml (DT 3.98±0.38 h), and D, 0.00062 IU/ml (DT 5.33±0.44 h). The range suitable for quantitative determination of penicillin G was between 0.00016 to 0.00062 IU/ml, and an equation for the regression line was obtained: DT=4000×(penicillin G)+2.8. The precision of the conductimetric technique (six replicates) was high; coefficients of variance were 2.2, 5.3, 9.5, and 8.3% for penicillin G concentrations of 0.00008, 0.00016, 0.00031, and 0.00062 IU/ml, respectively. The increased coefficients of variance at higher antibiotic concentrations might be partly due to the much smaller slopes of the conductance curves (FIG. 3; curves D, E, and F). The small slopes made the determination of an accurate DT more difficult, resulting in larger errors and hence higher coefficients of variance. However, for all concentrations in the quantitative range (0.00016 to 0.00062 IU/ml), the coefficients of variance were <10% and were acceptable for trace analysis In any event, because of the high sensitivity and the relatively small range useful for quantitative analysis by the conductimetric technique (FIG. 4), milk samples having penicillin G concentrations >0.00062 IU/ml should be appropriately diluted for quantitative purposes.

Detection of the Presence of Penicillin G in 12 Milk Samples

After establishment of the conditions for conductance measurement, the technique was applied to test 12 market milk products, including six dry milk powders and six infant formulas.

10 g of each product was added to 90 ml of deionized water and serially twofold diluted with the negative control milk (Difco). Each diluted sample was subdivided into two portions: one portion (1 ml) was heated at 82° C. for 3 min, cooled immediately in an ice bath, and treated with 0.1 ml of β-lactamase (165 U/ml) at 37° C. for 30 min. Following the addition of 1 ml of each sample (positive and negative controls, and enzyme-treated and untreated samples) into the conductance cell, 2 ml of PM indicator agar containing 1% *B. stearothermophilus* spore were added and mixed thoroughly. Cells were incubated at 55° C. for the measuring of conductance change. Penicillin G in the milk products was also determined by the *B. stearothermophilus* disc assay. See Bishop, J. R., G. F. Senyk, and S. E. Duncan (1992), "Detection of antibiotic/drug residues in milk and dairy products" in Standard Methods for the Examination of Dairy Products. 16 ed. R. T. Marshall, ed. Am. Publ. Health Assoc., Washington, D.C., which is hereby incorporated by reference.

As shown in Table 1, six samples (three dry milk products and three infant formulas, i.e., milk powders A, B and C, and infant formulas A, D and E) were contaminated with β-lactam antibiotics, ranging from 0.01 to 0.08 IU/g (potency equivalent to penicillin G), and were confirmed by the treatment with β-lactamase. Three other samples (milk powders E and F, and infant formula F) were contaminated by inhibitors other than β-lactam antibiotics, because the DT's could not be restored or shortened after treatment with β-lactamase. However, because of the relatively low sensitivity of the *B. stearothermophilus* disc assay (detection limit 0.005 IU/ml; i.e., 0.05 IU/g milk powder), only one sample (infant formula E) was able to produce inhibition zones by the disc assay. Obviously, the present conductimetric method can detect low concentrations of penicillin G in milk products that would be negative by the currently used assays.

TABLE 1

Detection of penicillin G in milk powders and infant formulas

| Product | Detection time[1] (h) | β-Lactam antibiotics[2] (IU/g) |
|---|---|---|
| Milk powder | | |
| A | >24 | .057 |
| B | >24 | .045 |
| C | >24 | .064 |
| D | 2.6 | ND[3] |
| E | >24 | U[4] |
| F | >24 | U |
| Infant formula | | |
| A | >24 | .010 |
| B | 2.6 | ND |
| C | 2.6 | ND |
| D | >24 | .023 |
| E[5] | >24 | .080 |
| F | >24 | U |

[1] Sample reconstituted 1:10 (wt/vol) in deionized water.
[2] Potency equivalent to penicillin G.
[3] No inhibitors detected.
[4] Containing unidentified inhibitors other than β-lactams.
[5] Except infant formula E, other samples were negative by the *Bacillus stearothermophilus* disc assay Other Embodiments From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for determining the concentration of an antimicrobial compound in a sample, the method comprising the steps of:

adding the sample to a culture medium containing a microorganism;

growing said microorganism in the culture medium, the growth of said microorganism being susceptible to inhibition by the compound;

measuring an electrical parameter of said culture medium over a period of time;

determining a first time point at which an accelerating change of said electrical parameter occurs, said change resulting from the growth of said microorganism; and comparing said first time point with a plurality of time points to determine the concentration of the compound, wherein each of said plurality of time points is determined under the same condition as said first time point is determined except that the compound is present in said culture medium at different known concentrations, and, further, preparing a linear curve from said plurality of time points in which a linear relationship exists between said plurality of time points and their corresponding concentrations and determining the concentration of said antimicrobial compound in said sample from said linear curve.

2. The method of claim 1, wherein said microorganism is a bacterium.

3. The method of claim 2, wherein said bacterium is *Bacillus stearothermophilus*.

4. The method of claim 3, wherein said compound is selected from the group consisting of the β-lactam family, the tetracycline family, the erythromycin family, the aminoglycoside family, the novobiocin family, the chloramphenicol family, or the sulfonamide family.

5. The method of claim 4, wherein said compound is of the β-lactam family.

6. The method of claim 5, wherein said compound is penicillin G.

7. The method of claim 5, further comprising the step of comparing said first time point with a second time point which is determined under the same condition as said first time point is determined except that β-lactamase is added to said culture medium, thereby confirming the presence of a lactam antibiotic.

8. The method of claim 6, wherein the sensitivity of said method is 0.00016 IU/ml.

9. The method of claim 1, wherein said electrical parameter is conductance.

10. The method of claim 2, wherein said electrical parameter is conductance.

11. The method of claim 3, wherein said electrical parameter is conductance.

12. The method of claim 5, wherein said electrical parameter is conductance.

13. The method of claim 8, wherein said electrical parameter is conductance.

14. The method of claim 1, further comprising the step of comparing said first time point with a second time point which is determined under the same condition as said first time point is determined except that a reagent capable of abolishing the antimicrobial activity of the compound is added to said culture medium, thereby confirming the presence of the compound.

15. The method of claim 14, wherein said microorganism is a bacterium.

16. The method of claim 15, wherein said electrical parameter is conductance.

17. A method for testing the resistance of a microorganism to an antimicrobial compound, said method comprising the steps of:

growing a microorganism to be tested in a culture medium containing the compound;

measuring an electrical parameter of said culture medium over a period of time;

determining a first time required for an accelerating change of said electrical parameter resulting from the growth of said tested microorganism to occur; and comparing said first time with a second time which is determined under the same condition as said first time is determined except that the compound is absent from said culture medium, whereby said tested microorganism is defined to be resistant to the compound when said first time is equal to said second time and defined to be not resistant to the compound when said first time is greater than said second time.

18. The method of claim 17, wherein said tested microorganism is a bacterium.

19. The method of claim 17, wherein said electrical parameter is conductance.

20. The method of claim 18, wherein said electrical parameter is conductance.

* * * * *